(12) United States Patent
Franklin

(10) Patent No.: US 7,700,608 B2
(45) Date of Patent: *Apr. 20, 2010

(54) QUINAZOLINE DERIVATIVES AND THEIR USE IN THE TREATMENT OF THROMBOCYTHEMIA

(75) Inventor: Richard Franklin, Hampshire (GB)

(73) Assignee: Shire Holdings AG, Zug (CH)

( * ) Notice: Subject to any disclaimer, the term of this patent is extended or adjusted under 35 U.S.C. 154(b) by 1059 days.

This patent is subject to a terminal disclaimer.

(21) Appl. No.: 11/197,775

(22) Filed: Aug. 3, 2005

(65) Prior Publication Data

US 2006/0052601 A1 Mar. 9, 2006

Related U.S. Application Data

(60) Provisional application No. 60/598,437, filed on Aug. 4, 2004.

(51) Int. Cl.
| A61K 31/517 | (2006.01) |
| A61K 31/505 | (2006.01) |
| A61P 7/02 | (2006.01) |
| C07D 471/04 | (2006.01) |
| C07D 471/14 | (2006.01) |
| C07D 471/16 | (2006.01) |
| C07D 239/84 | (2006.01) |

(52) U.S. Cl. .................... 514/266.4; 514/267; 544/250; 544/292

(58) Field of Classification Search .............. 514/266.4, 514/267; 544/292, 250
See application file for complete search history.

(56) References Cited

U.S. PATENT DOCUMENTS

| 1,947,926 A | 2/1934 | Steindorff et al. |
| 2,256,999 A | 9/1941 | Castner |
| 2,469,695 A | 5/1949 | McNally |
| 2,608,584 A | 8/1952 | Sprules et al. |
| 2,732,403 A | 1/1956 | Surrey |
| 2,862,966 A | 12/1958 | Surrey |
| 2,883,435 A | 4/1959 | Welch |
| 3,313,854 A | 4/1967 | Levy |
| 3,928,476 A | 12/1975 | Shimada et al. |
| 3,932,407 A | 1/1976 | Beverung, Jr. et al. |
| 3,983,119 A | 9/1976 | Beverung, Jr. et al. |
| 3,983,120 A | 9/1976 | Beverung et al. |
| 3,988,340 A | 10/1976 | Partyka et al. |
| 4,036,838 A | 7/1977 | Vogel et al. |
| 4,048,168 A | 9/1977 | Yamamoto et al. |
| 4,146,718 A | 3/1979 | Jenks et al. |
| 4,179,560 A | 12/1979 | Yamamoto et al. |
| 4,202,974 A | 5/1980 | Yamamoto et al. |
| 4,208,521 A | 6/1980 | Crenshaw et al. |
| 4,256,748 A | 3/1981 | Chodnekar et al. |
| 4,357,330 A | 11/1982 | Fleming, Jr. et al. |
| 4,390,540 A | 6/1983 | Chodnekar et al. |
| 4,444,777 A | 4/1984 | Fleming, Jr. et al. |
| RE31,617 E | 6/1984 | Beverung, Jr. et al. |
| 4,455,311 A | 6/1984 | Kienzle |
| 4,610,987 A | 9/1986 | Ishikawa |
| 4,808,405 A | 2/1989 | Smith et al. |
| 4,837,239 A | 6/1989 | Benjamin et al. |
| 4,847,276 A | 7/1989 | Yarrington |
| 5,043,327 A | 8/1991 | Freyne et al. |
| 5,133,972 A | 7/1992 | Ferrini et al. |
| 5,306,709 A | 4/1994 | Gewirtz |
| 5,334,384 A | 8/1994 | Mannix et al. |
| 5,391,737 A | 2/1995 | Reiter et al. |
| 5,801,245 A | 9/1998 | Lang |
| 5,874,437 A | 2/1999 | Garvey et al. |
| 6,024,975 A | 2/2000 | D'Angelo et al. |
| 6,037,346 A | 3/2000 | Doherty, Jr. et al. |
| 6,110,471 A | 8/2000 | Conti et al. |
| 6,156,753 A | 12/2000 | Doherty, Jr. et al. |
| 6,194,420 B1 | 2/2001 | Lang |
| 6,297,243 B1 | 10/2001 | Groendahl |
| 6,299,900 B1 | 10/2001 | Reed et al. |
| 6,331,543 B1 | 12/2001 | Garvey et al. |
| 6,376,242 B1 | 4/2002 | Hanson |
| 6,388,073 B1 | 5/2002 | Lang et al. |
| 6,403,597 B1 | 6/2002 | Wilson et al. |
| 6,548,490 B1 | 4/2003 | Doherty, Jr. et al. |
| 6,548,529 B1 | 4/2003 | Robl et al. |
| 6,585,995 B1 | 7/2003 | Hanson |
| 6,653,500 B2 | 11/2003 | Lang et al. |

(Continued)

FOREIGN PATENT DOCUMENTS

AT    A273/2004    1/2005

(Continued)

OTHER PUBLICATIONS

Wang, G. et. al., "Comparison of the biological activities...", British Journal of Pharmacology, 2005, vol. 146, pp. 324-332.*

(Continued)

Primary Examiner—James O Wilson
Assistant Examiner—Tamthom N Truong
(74) Attorney, Agent, or Firm—Darby & Darby P.C.; Shelly M. Fujikawa

(57) ABSTRACT

A method for the treatment of thrombocythemia in a subject comprising administering a therapeutically effective amount of compounds having the formulas (I) through (III) or equilibrating forms thereof.

18 Claims, 2 Drawing Sheets

U.S. PATENT DOCUMENTS

| | | | |
|---|---|---|---|
| 2002/0004065 | A1 | 1/2002 | Kanios |
| 2002/0004498 | A1 | 1/2002 | Doherty et al. |
| 2003/0114673 | A1 | 6/2003 | Lang |
| 2003/0134861 | A1 | 7/2003 | Doherty et al. |
| 2003/0181461 | A1 | 9/2003 | Lautt et al. |
| 2004/0014761 | A1 | 1/2004 | Place et al. |
| 2004/0087486 | A1 | 5/2004 | Hanson |
| 2004/0087546 | A1 | 5/2004 | Zeldis |
| 2004/0209907 | A1 | 10/2004 | Franklin |
| 2005/0049293 | A1 | 3/2005 | Lautt |
| 2005/0119272 | A1 | 6/2005 | Lautt et al. |
| 2006/0292213 | A1* | 12/2006 | Gerber et al. ............... 424/451 |

FOREIGN PATENT DOCUMENTS

| | | |
|---|---|---|
| DE | 2832138 | 1/1979 |
| DE | 199 35 209 A1 | 2/2001 |
| EP | 0021338 | 1/1981 |
| EP | 0046267 | 2/1982 |
| EP | 0054180 | 6/1982 |
| EP | 0153152 | 8/1985 |
| EP | 0 205 208 | 12/1986 |
| EP | 0 205 280 | 12/1986 |
| EP | 0406958 | 1/1991 |
| EP | 0514917 | 11/1992 |
| EP | 0546697 A2 | 6/1993 |
| EP | 994114 | 4/2000 |
| JP | 4719261 | 6/1972 |
| JP | 01258658 | 10/1989 |
| WO | WO-9308798 | 5/1993 |
| WO | WO-9309794 | 5/1993 |
| WO | WO94/28902 | 12/1994 |
| WO | WO96/16644 | 6/1996 |
| WO | WO98/10765 | 3/1998 |
| WO | WO-9938496 | 8/1999 |
| WO | WO-0048636 | 8/2000 |
| WO | WO01/21259 | 3/2001 |
| WO | WO-0121163 | 3/2001 |
| WO | WO01/40196 | 6/2001 |
| WO | WO01/41807 | 6/2001 |
| WO | WO02/08228 | 1/2002 |
| WO | WO-02062322 | 8/2002 |
| WO | WO03/000343 | 1/2003 |
| WO | WO03/061638 | 7/2003 |
| WO | WO03/061648 | 7/2003 |
| WO | WO-2004012700 | 2/2004 |
| WO | WO2004/037262 | 5/2004 |
| WO | WO-2004043336 | 5/2004 |
| WO | WO-2004043464 | 5/2004 |
| WO | WO2004/063172 | 7/2004 |
| WO | WO 2004/063172 | 7/2004 |
| WO | WO2004/064841 | 8/2004 |
| WO | WO2005/025570 | 3/2005 |
| WO | WO-2005048979 | 6/2005 |
| WO | WO-2005065639 | 7/2005 |
| WO | WO2006017822 | 2/2006 |
| WO | WO-2006017822 | 2/2006 |

OTHER PUBLICATIONS

Abe Andes et al., "Inhibition of platelet production induced by an antiplatelet drug, anagrelide, in normal volunteers." Thromb. Haemost., 1984, 52:325-8.

Agrylin Product Monograph, Shire Laboratories, 2003.

Decision on FDA Citizen Petition No. 2004P-0365 by the FDA, Apr. 18, 2005.

Doherty, "Oral, Transdermal and Transurethral Therapies for Erectile Dysfunction, in Male Infertility and Dysfunction," Hellstrom ed., Ch. 33, 1997, Springer-Verlag: New York.

Erusalimsky et al., "Is the platelet lowering activity of anagrelide mediated by its major metabolite 2-amino-5,6-dichloro-3,4-dihydroquinazoline (RL603)?" Exp. Hematol., 2002, 30:625-627.

European Agency for the Evaluation of Medicinal Products (EMEA): Scientific Discussion of European Public Assessment Report (EPAR) Xagrid [http://www.emea.eu.int/humandocs/PDFs/EPAR/Xagrid/136504en6.pdf] European Agency for the Evaluation of Medicinal Products, 2004.

Food and Drug Administration Citizen Petition No. 2004P-0365 on behalf of Shire US, Inc., dated Aug. 13, 2004.

Gaver et al., "Disposition of anagrelide, an inhibitor of platelet aggregation," Clin. Pharmacol. Ther., 1981, 29:381-386.

Green et al., "Management of the myeloproliferative disorders : distinguishing data from dogma." Hematol. J., 2004, 5 Suppl. 3:S126-132.

Jones et al., "Inhibitors of cyclic AMP phosphodiesterase. 1. Analogues of cilostamide and anagrelide," J. Med. Chem., 1987, 30:295-303.

Kienzle et al., "1,5-Dihydroimidazoquinazolinones as blood platelet aggregation inhibitors," Eur. J. Med. Chem., 1982, 17:547-556.

Kienzle et al., "Die synthese von 2,3,4,5-1$H$tetrahydroimidazo-[2,1-$b$]chinazolin-2,5-dionen und analogen 2,3,4,5-1$H$-tetrahydroimidazo[1,2-$a$]thieno[2,3-$d$](bzw. [3,2-$d$])-pyrimidin-2,5-dionen," Helv. Chim. Acta, 1983, 66:148-157.

Kelly and Smith, *"Pharmacological Treatment of Heart Failure,"* in Goodman and Gilman's *"The Pharmacological Basis of Therapeutics"*, 1996, 9$^{th}$ ed., Ch. 34, McGraw-Hill: New York.

Lane et al., "Anagrelide metabolite induces thrombocytopenia in mice by inhibition of megakaryocyte maturation and endoreplication without inducing platelet aggregation," Blood, 1999, 94:701a Supp. 1 (Part 1 of 2) [abstract #3097].

Martinez et al., "3,4-Dihydroquinolin-2(1H)-ones as combined inhibitors of thromboxane A2 synthase and cAMP phosphodiesterase," J. Med. Chem., 1992, 35:620-628.

Mazur et al., "Analysis of the mechanism of anagrelide-induced thrombocytopenia in humans." Blood, 1992, 79:1931-1937.

Meanwell et al., "1,3-Dihydro-2H-imidazo[4,5-b]quinolin-2-ones—inhibitors of blood platelet cAMP phosphodiesterase and induced aggregation," J. Med. Chem., 1991, 34:2906-2916.

Meanwell et al., "Inhibitors of blood platelet cAMP phosphodiesterase. 2. Structure-activity relationships associated with 1,3-dihydro-2H-imidazo[4,5-b]quinolin-2-ones substituted with functionalized side chains," J. Med. Chem., 1992, 35:2672-2687.

Oertel, "Anagrelide, a selective thrombocytopenic agent." Am. J. Health Syst. Pharm., 1998, 55:1979-86.

Pescatore et al., "Anagrelide: a novel agent for the treatment of myeloproliferative disorders." Expert Opin. Pharmacother., 2000, 1:537-46.

Petitt et al., "Anagrelide for control of thrombocythemia in polycythemia and other myeloproliferative disorders." Semin. Hematol., 1997, 34:51-4.

Response to Food and Drug Administration Citizen Petition No. 2004P-0365 by Mylan Pharmaceuticals, dated Sep. 8, 2004.

Response to Food and Drug Administration Citizen Petition No. 2004P-0365 on behalf of Barr Laboratories, dated Oct. 20, 2004.

Spencer and Brogden, "Anagrelide. A review of its pharmacodynamic and pharmacokinetic properties, and therapeutic potential in the treatment of thrombocythaemia." Drugs, 1994 47:809-22.

Stalder, "Metaboliten der 1,5-Dihydroimidazo[2,1-b]chinazolin-2(3H)-one. Synthese und Reaktionen einiger 1,5-Dihydro-3-hydroxyimidazo[2,1-b]chinazolin-2(3H)-one," Helv. Chim. Acta, 1986, 69:1887-1897 (and translation).

Storen and Tefferi, "Long-term use of anagrelide in young patients with essential thrombocythemia." Blood, 2001, 97:863-866.

Trapp et al., "Anagrelide for treatment of patients with chronic myelogenous leukemia and a high platelet count." Blood Cells Mol. Dis., 1998, 24:9-13.

Venuti et al., "Inhibitors of cyclic AMP phosphodiesterase. 2. Structural Variations of N-cyclohexyl-N-methyl-4-[C1, 2, 3, 5-tetrahydro-2-oximidazo [2,1-b] quinazolin-7-yl)-oxy] butyramide," J. Med. Chem., 1987, 30: 303-318.

Venuti et al., "Inhibitors of cyclic AMP phosphodiesterase. 3. Synthesis and biological evaluation of pyrido and imidazolyl analogues of 1,2,3,5-tetrahydro-2-oxoimidazo[2,1-b]quinazoline," J. Med. Chem., 1988, 31:2136-2145.

Wang et al., "Comparison of the biological activities of anagrelide and its major metabolites in haematopoietic cell cultures," Br. J. Pharmacol., 2005, 1-9, EPUB Jul. 25, 2005 (now Br. J. Pharmacol., 2005, 146:324-332).

Lane et al., "Anagrelide metabolite induces thrombocytopenia in mice by inhibiting megakaryocyte maturation without inducing platelet aggregation," Exp. Hematol., 2001, 29:1417-1424.

International Search Report for PCT/US05/28086 mailed Jun. 14, 2006.

Citizen Petition, Arnall Golden Gregory LLP, Aug. 13, 2004, 159 pages.

Wang, Guosu, et al., "Comparison of the Biological Activities of Anagrelide and its Major Metabolites in Haematopoietic Cell Cultures," British Journal of Pharmacology 2005, vol. 146:324-332.

Bell, Andrew S., et al. "7-Heteroaryl-1,2,3,5-tetrahydroimidazo[2,1-b]quinazolin-2(1H)-one Derivatives with Cardiac Stimulant Activity," Journal of Medicinal Chemistry, 1989, vol. 32, No. 9, pp. 2042-2049 (8 pages).

Kienzle, Frank, et al. "1,5-Dihydroimidazoquinazolinones as Blood Platelet Aggregation Inhibitors," European Journal of Medicinal Chemistry, 1982-17, No. 6, pp. 546-556 (10 pages).

Imidazo[2,1-b]quinazolin-2(3H)-one, 1,5-dihydro-3,3-dimethyl-,monohydrochloride (9CI), as referenced in European Journal of Medicinal Chemistry (1982), 17(6), 547-56 (1 page).

Imidazo[2,1-b]quinazolin-2(3H)-one, 1,5-dihydro-3,3,6-trimethyl-, monohydrochloride (9CI), as referenced in European Journal of Medicinal Chemistry (1982), 17(6), 547-56 (1 page).

Imidazo[2,1-b]quinazolin-2(3H)-one, 1,5-dihydro-3,3,6-trimethyl-, as supplied by Chemstep, France. Catalog Publication Date Jun. 19, 2007 (1 page).

Imidazo[2,1-b]quinazolin-2(3H)-one, 1,5-dihydro-3,3-dimethyl-, as supplied by Chemstep, France. Catalog Publication Date Jun. 19, 2007 (1 page).

A signed Declaration pursuant to 37 C.F.R. §1.132 by Dr. Richard Franklin submitted in U.S. Appl. No. 10/762,566 on Sep. 19, 2007 and Exhibit 1 to the Declaration (the curriculum vitae for Dr. Richard Franklin), 8 pgs.

Agrylin (anagrelide hydrochloride), Product Monograph, Roberts Pharmaceutical Corp.; 1997.

Barbui, Tiziano, et al., "Practice guidelines for the therapy of essential thrombocythemia. A statement from the Italian society of Hematology, the Italian Society of Experimental Hematology and the Italian Group for Bone Marrow Transplantation." Haematologica 2004; 89:215-232.

Bell, Andrew S., et al. "7-Heteroary1-1,2,3,5-tetrahydroimidazo[2,1-b]quinazolin-2(1H)-one Derivatives with Cardiac Stimulant Activity," Journal of Medicinal Chemistry, 1989, vol. 32, No. 9, pp. 2042-2049 (8 pages).

Blood; Journal of the American Society of Hematology; W. R. Saunders Company; vol. 94; No. 10; Supplement 1 (Part 1 of 2); Nov. 15, 1999; p. 701a.

Citizen Petition, Amall Golden Gregory LLP, Aug. 13, 2004, 159 pgs.

Cohen-Solal et al., Thromb. Haemost. 1997, 78:37-41, p. 18, 131 of 5096 and p. 27, 19 of 3796.

Cramer et al., Blood, 1997, 89:2336-46 p. 18,131 of 5096 and p. 27, 19 of 3796.

Dörwald, F. Zaragoza. "Side Reactions in Organic Synthesis: A Guide to Successful Synthesis Design," Weinheim: Wiley-VCH Verlag GmbH & Co. KGaA, 2005, Preface.

FDA Citizen Petition No. 2004P-0365 on behalf of Shire US, Inc., Aug. 13, 2004.

Griesshammer, Martin et al. "Current treatment practice for essential thrombocythaemia in adults" Exp. Opin. Pharmacother., 2001, 2: 385-393.

Imidazo[2,1-b]quinazolin-2(3H)-one, 1,5-dihydro-3,3-dimethyl-, monohydrochloride (9CI), as referenced in European Journal of Medicinal Chemistry (1982), 17(6), 547-56 (1 page).

International Search Report in connection with International Application No. PCT/CA2004/000096, dated Jun. 23, 2004.

International Search Resort for PCT/US05/28086 mailed Jun. 14, 2006.

Jordan, V.C. "Nature Reviews: Drug Discovery," 2, 2003, p. 205.

Morrison & Boyd, "Organic Chemistry," 3rd Ed. 1975, 344-347; 387-388.

Osinski, M., et al. "Inhibition of platelet-derived growth factor-induced mitogenesis by phosphodiesterase 3 inhibitors: Role of protein kinase A in vascular smooth muscle cell mitogenesis," Biochemical Pharmacology 2000, vol. 60, No. 3, pp. 381-387.

Petrides, P., et al. "Anagrelide, a Novel Platelet Lowering Option in Essential Thrombocythaemia: Treatment Experience in 48 Patients in Germany," European Journal of Haematology, vol. 61, 1998, p. 71-76.

Rafii S. et al. "In Response:—Is the platelet lowering activity of anagrelide mediated by its major metabolite 2-amino-5, 6-dichloro-3, 4-dihydroquinazoline (RL603)?" Experimental Hematology (Charlottesville). vol. 30, No. 7, p. 626-627 (2002).

Solberg, L. A. et al. "The Effects of Anagrelide on Human Megakaryocytopoiesis." British Journal of Haematology. vol. 99, No. 1, p. 174-180 (1997).

Souhami, R.L., et al., "Textbook of Internal Medicine," Churchill-Livingstone, p. 1043, table 25.53, 1997.

Tefferi, A., et al., "Spotlight Review—Classification and Diagnosis of myeloproliferative neoplasms: The 2008 World Health Organization criteria and point-of-care diagnostic algorithms," 2008 Nature Publishing Group. Table 1.

Vippagunta, S., et al. "Advanced Drug Delivery Reviews," 48, 2001, p. 18.

* cited by examiner

QUINAZOLINE DERIVATIVES AND THEIR USE IN THE TREATMENT OF THROMBOCYTHEMIA

CROSS-REFERENCE TO RELATED APPLICATION

Priority is claimed under 35 U.S.C. §119(e) to co-pending U.S. Provisional Patent Application Ser. No. 60/598,437, filed on Aug. 4, 2004. The contents of this priority application are hereby incorporated into the present disclosure by reference and in their entirety.

FIELD OF THE INVENTION

The present invention relates to compounds which are useful for treating thrombocythemia. The present invention also relates to compounds that are useful for reducing platelet counts.

BACKGROUND OF THE INVENTION

Thrombocythemia is a chronic disorder associated with increased or abnormal production of blood platelets. Since platelets are involved in blood clotting, their abnormal production can result in the inappropriate formation of blood clots or in bleeding, with the consequence that patients' risk of gastrointestinal bleeding, heart attack and stroke is increased.

Anagrelide is a quinazoline derivative phosphodiesterase inhibitor used for the treatment of essential thrombocythemia and various other myeloproliferative disorders. Anagrelide was approved and launched in 1997 for the treatment of essential thrombocythemia in the US and Canada. In December 1998, the US FDA approved an expanded label for anagrelide—specifically, for the treatment of patients with thrombocythemia secondary to myeloproliferative disorders, including polycythemia vera (PV) and chronic myelogenous leukemia (CML).

A compound encompassed by the present invention is 3-hydroxyanagrelide. This is a metabolite of anagrelide (see, for example, U.S. patent application Ser. No. 10/762,566 published as U.S. Pub. No. 20040209907).

Various metabolites of anagrelide have been studied in the literature: Erusalimsky et al. (2002) Is the platelet lowering activity of anagrelide mediated by its major metabolite 2-amino-5,6-dichloro-3,4-dihydroquinazoline (RL603)? Exp Hematol. 30:625-7; Lane et al. (2001) Anagrelide metabolite induces thrombocytopenia in mice by inhibiting megakaryocyte maturation without inducing platelet aggregation. Exp Hematol. 29:1417-241; and Gaver et al. (1981) Disposition of anagrelide, an inhibitor of platelet aggregation. Clin Pharmacol Ther. 29:381-6.

It is among the objects of the present invention to provide compounds related to anagrelide that may be used for treating thrombocythemia.

SUMMARY OF THE INVENTION

In one embodiment, the present invention provides a compound that is

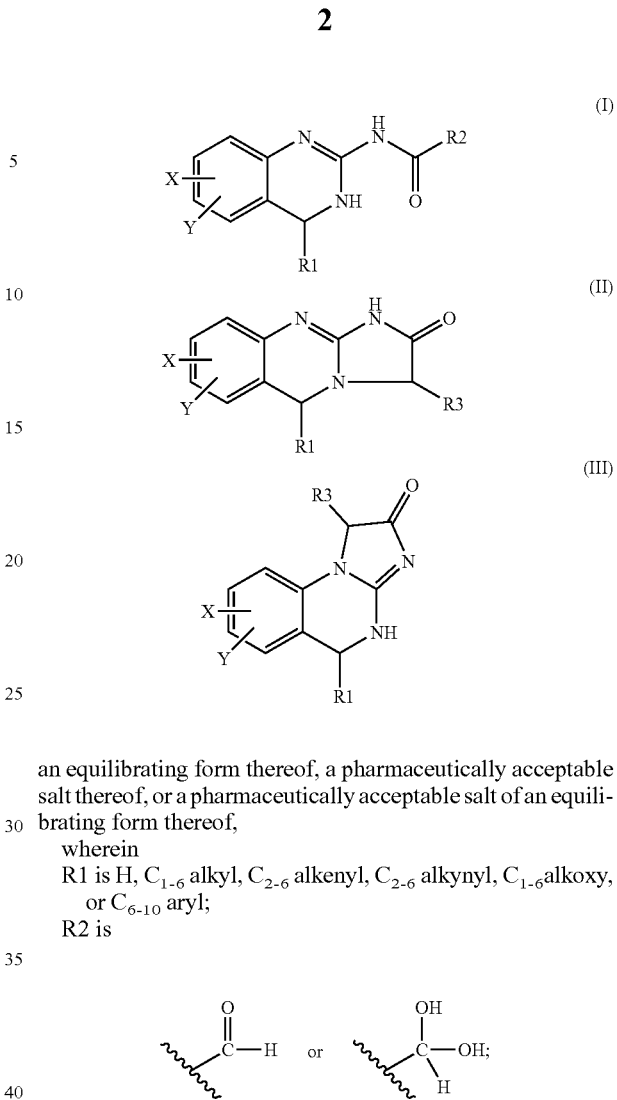

an equilibrating form thereof, a pharmaceutically acceptable salt thereof, or a pharmaceutically acceptable salt of an equilibrating form thereof,
wherein
R1 is H, $C_{1-6}$ alkyl, $C_{2-6}$ alkenyl, $C_{2-6}$ alkynyl, $C_{1-6}$ alkoxy, or $C_{6-10}$ aryl;
R2 is R3 is OH, Halogen, SH, O—$C_{1-6}$ alkyl or an hydroxyl mimetic group; and
X and Y are independently H or halogen.

Preferred of the above compounds include the X and Y substituents on the 5 and 6 positions of the benzyl ring.

The compounds of formulas (I) through (III) are useful in the treatment of thrombocythemia and in the reduction of platelets. The compounds of formulas (I) through (III) may be used in combination with at least one other therapeutic agent.

The present invention also provides for a pharmaceutical formulation comprising a compound of any of formulas (I) through (III) with a pharmaceutically acceptable carrier or excipient.

In a further embodiment, there is provided the use of a compound of formulas (I) through (III) for the manufacture of a medicament for the treatment of thrombocythemia.

DETAILED DESCRIPTION OF THE INVENTION

Figure 1:
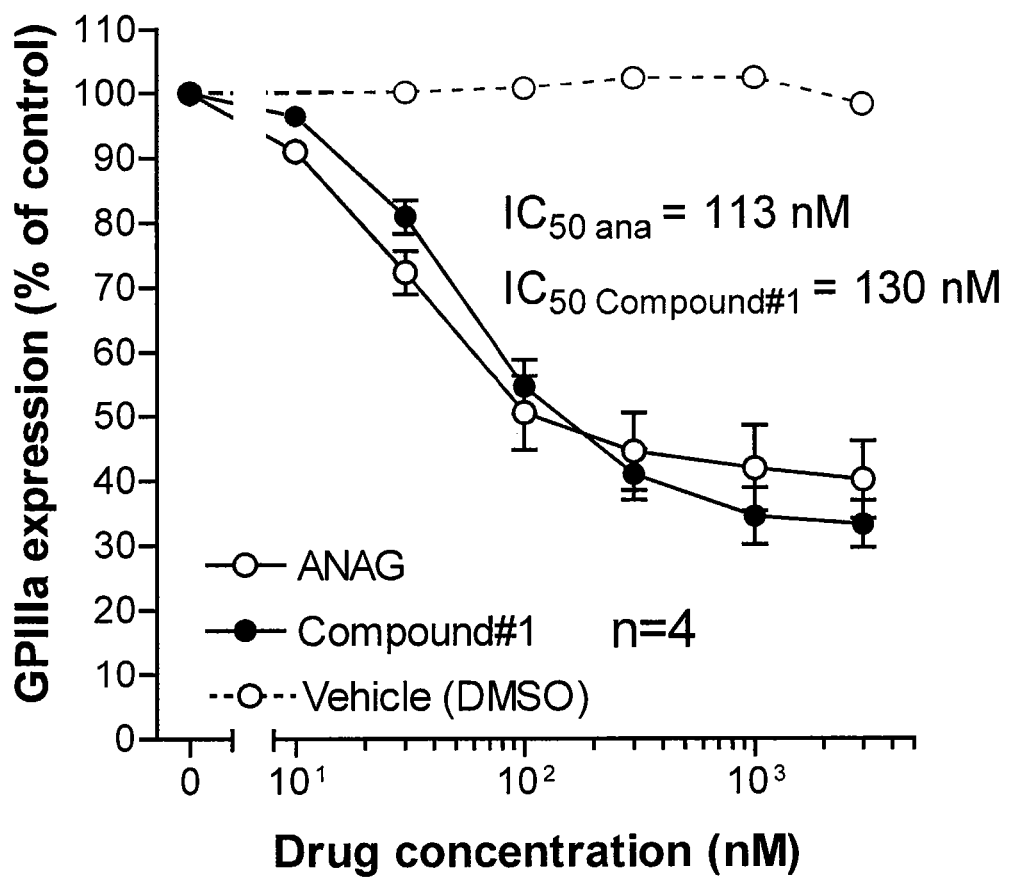
FIG. 1 is a dose-response graph comparing the effects of anagrelide and Compound #1 on TPO-induced megakaryocytic (MK) maturation as more fully described in Example 3 below.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

In one embodiment of the present invention, compounds of the present invention comprise those wherein the following embodiments are present, either independently or in combination.

In one embodiment, the present invention provides a compound of the formula

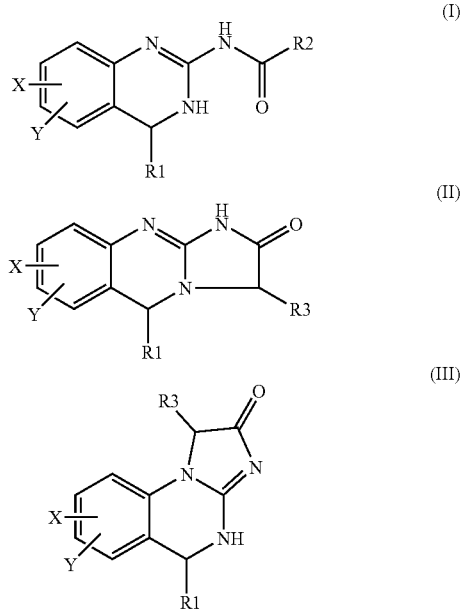

an equilibrating form thereof, a pharmaceutically acceptable salt thereof, or a pharmaceutically acceptable salt of an equilibrating form thereof,
wherein
R1 is H, $C_{1-6}$ alkyl, $C_{2-6}$ alkenyl, $C_{2-6}$ alkynyl, $C_{1-6}$ alkoxy, or $C_{6-10}$ aryl;
R2 is

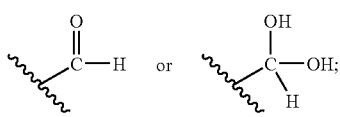

R3 is OH, Halogen, SH, O—$C_{1-6}$ alkyl or an hydroxyl mimetic group; and
X and Y are independently H or halogen.
Preferred embodiments include the X and Y substituents on the 5 and 6 positions of the benzyl ring.
In one embodiment, R1 is H or $C_{1-6}$ alkyl. In another embodiment, R1 is H or $CH_3$. In another embodiment, R1 is H.

In one embodiment, R3 is OH or O—$C_{1-6}$ alkyl. In another embodiment, R3 is OH or $OCH_3$. In another embodiment, R3 is OH.

In one embodiment, X is H or halogen. In another embodiment, X is H. In another embodiment, X is Cl. In another embodiment, Y is H or Cl. In another embodiment, Y is H. In another embodiment, Y is Cl.

In one embodiment, the thrombocythemia treated is associated with myeloproliferative blood disorders.

In one embodiment, the thrombocythemia is associated with essential thrombocythemia (ET), chronic myelogenous leukemia (CML), polycythemia vera (PV), agnogenic myeloid metaplasia (AMM) or sickle cell anemia (SCA).

In a further embodiment, the thrombocythemia is caused by ET, CML, PV, AMM, or SCA.

In a further embodiment, the compounds of formulas (I) through (III) can be used to reduce platelet count in a subject.

Compounds in accordance with the present invention include

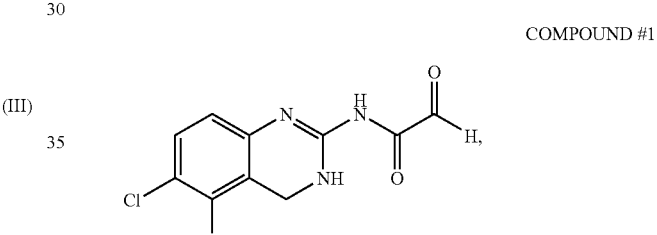

which is N-(5,6-dichloro-3,4-dihydroquinazolin-2-yl)-2-oxoacetamide;

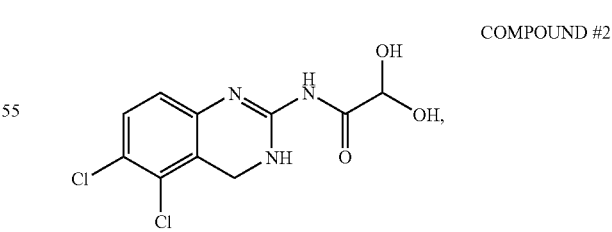

which is N-(5,6-dichloro-3,4-dihydroquinazolin-2-yl)-2-oxoacetamide hydrate;

COMPOUND #3

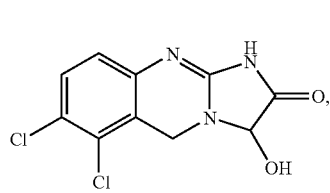

which is 6,7-dichloro-3-hydroxy-1,5-dihydro-imidazo[2,1-b]quinazolin-2-one;

COMPOUND #4

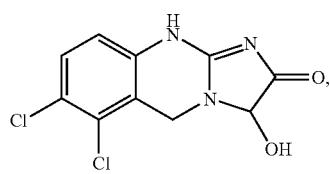

which is 6,7-dichloro-3-hydroxy-1,5-dihydro-imidazo[2,1-b]quinazolin-2-one; and

COMPOUND #5

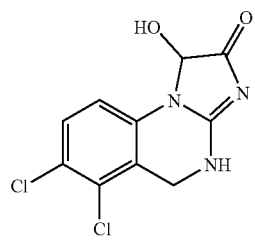

which is 6,7-dichloro-1-hydroxy-3,5-dihydro-imidazo[1,2-a]quinazolin-2-one.

In accordance with the present invention, the compounds are in substantially pure form.

As used in this application, the term "substantially pure form" means that the compounds are at least 80% pure, preferably at least 85% pure, more preferably at least 90% pure, more preferably still at least 95% pure, and most preferably at least 99% pure as determined by standard analytical methods.

Without being bound to any theory (an understanding of the mechanism is not necessary to practice the present invention, and the present invention is not limited to any particular mechanism), the present inventors believe the compounds of the present invention are equilibrating forms. The equilibrating forms of the compounds of the present invention are depicted as follows:

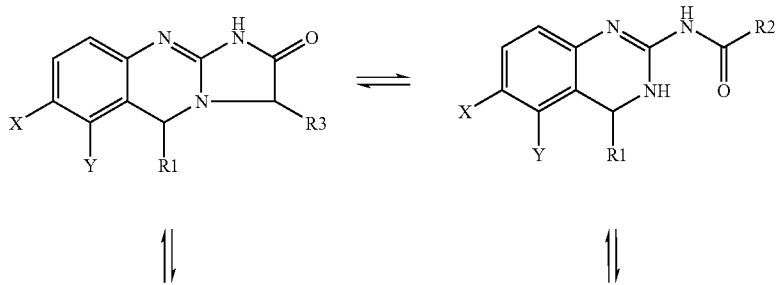

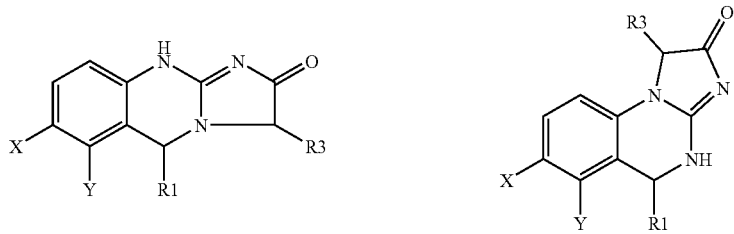

As used herein, the term "equilibrating form" includes tautomers of the compounds of formulas (I) through (III).

The equilibrating forms of the compounds of the invention can also be represented as follows:

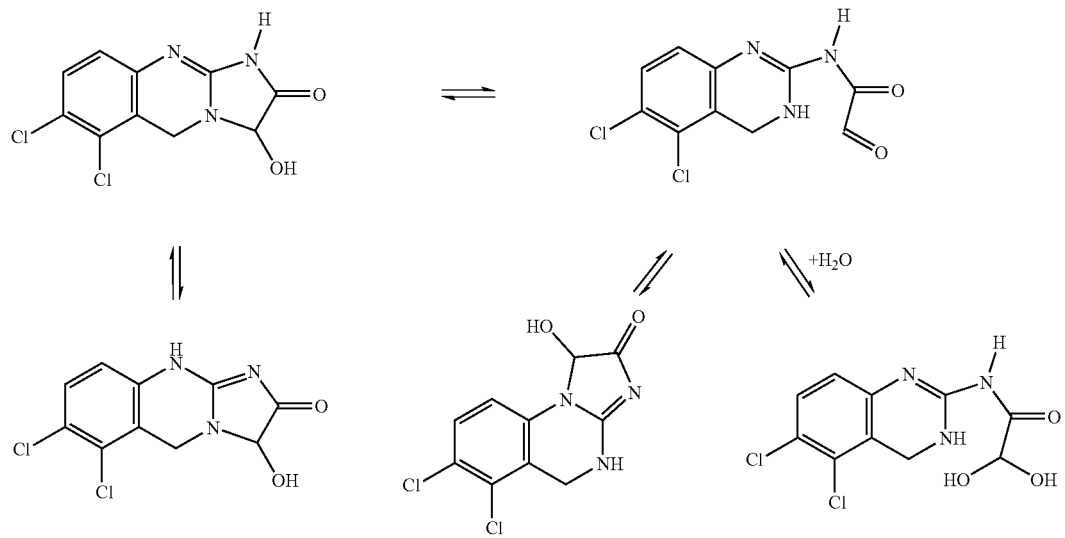

All such equilibrating forms are included in the scope of the present invention.

It will be appreciated by those of ordinary skill in the art that the compounds of formulas (I) through (III) may exist as tautomers or optical isomers. All equilibrating isomers and tautomers of such compounds are included in the scope of the present invention. The single optical isomer or enantiomer can be obtained by methods well known in the art, such as chiral HPLC, enzymatic resolution and chiral auxiliary, or can be stereoselectively synthesized.

As used herein, "hydroxymimetic" describes chemical functional groups related to the hydroxyl (—OH) group. These are functional groups that can act as a hydrogen bond donor and acceptor. Non-limiting examples of hydroxymimetic groups include —$NH_2$ and —SH.

There are also provided pharmaceutically acceptable salts of the compounds of the present invention. By the term "pharmaceutically acceptable salts" of the compounds of general formulas (I) through (III) those meant are those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium, and $NR_4+$ (where R is $C_{1-4}$ alkyl) salts.

As used in this application, the term "alkyl" represents an unsubstituted or substituted (by a halogen, nitro, $CONH_2$, COOH, O—$C_{1-6}$ alkyl, O—$C_{2-6}$ alkenyl, O—$C_{2-6}$ alkynyl, hydroxyl, amino, or COOQ, wherein Q is $C_{1-6}$ alkyl, $C_{2-6}$ alkenyl; $C_{2-6}$ alkynyl) straight chain, branched chain or cyclic hydrocarbon moiety (e.g. isopropyl, ethyl, fluorohexyl or cyclopropyl). The term alkyl is also meant to include alkyls in which one or more hydrogen atoms is replaced by a halogen, more preferably, the halogen is fluoro (e.g. —$CF_3$ or —$CH_2CF_3$)

As used herein, the terms "alkenyl" and "alkynyl" represent an alkyl (as defined above) containing at least one unsaturated group (e.g. allyl).

When there is a sulfur atom present, the sulfur atom can be at different oxidation levels: S, SO, or $SO_2$. All such oxidation levels are within the scope of the present invention.

Halogen herein means fluoro, chloro, bromo, and iodo.

"Treating" or "treatment" of a state, disorder or condition includes:

(1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving the disease, i.e., causing regression of the state, disorder or condition or at least one of its clinical or subclinical symptoms.

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

A subject in need thereof is an individual, for example a human or other mammal that would benefit by the administration of the compounds of the present invention.

The benefit to a subject to be treated is either statistically significant or at least perceptible to the patient or to the physician.

It will be appreciated that the amount of a compound of the invention required for use in treatment will vary not only with the particular compound selected but also with the route of administration, the nature of the condition for which treatment is required, and the age and condition of the patient and will be ultimately at the discretion of the attendant physician or veterinarian. In general, however, a suitable dose will be in the range of from about 0.001 to about 50 mg/kg of body weight per day, preferably of from about 0.001 to about 5 mg/kg of body weight per day, more preferably of from about 0.001 to about desirably 0.5 mg/kg of body weight per day, or most desirably from about 0.001 to about 0.1 mg/kg of body weight per day. In further embodiments, the ranges can be of from about 0.1 to about 750 mg/kg of body weight per day, in the range of 0.5 to 60 mg/kg/day, and in the range of 1 to 20 mg/kg/day.

The desired dose may conveniently be presented in a single dose or as divided doses administered at appropriate intervals, for example as two, three, four or more doses per day. If the compounds are administered transdermally or in extended release form, the compounds could be dosed once a day or less.

The compound is conveniently administered in unit dosage form, for example containing 0.1 to 50 mg, conveniently 0.1 to 5 mg, or most conveniently 0.1 to 5 mg of active ingredient per unit dosage form. In yet a further embodiment, the compound can conveniently be administered in unit dosage form, for example containing 10 to 1500 mg, preferably 20 to 1000 mg, or more preferably 50 to 700 mg of active ingredient per unit dosage form.

Ideally the active ingredient should be administered to achieve peak plasma concentrations of the active compound of from about 0.01 to about 5 µM, from about 0.01 to about 1 µM, from about 1 to about 75 µM, from about 2 to 50 µM, or from about 3 to about 30 µM. This may be achieved, for example, by the intravenous injection of a 0.1 to 5% solution of the active ingredient, optionally in saline, or orally administered as a bolus containing about 0.1 to about 5 mg or about 1 to about 500 mg of the active ingredient. Desirable blood levels may be maintained by a continuous infusion to provide about 0.0001 to about 1.0 mg/kg/hour or about 0.0001 to about 0.5 mg/kg/hour or by intermittent infusions containing about 0.001 to about 0.1 mg/kg of the active ingredient. In a further embodiment, desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical, it is preferable to present the active ingredient in a pharmaceutical formulation. The invention thus further provides a pharmaceutical formulation comprising a compound of formulas (I) through (III) or an equilibrating form thereof together with one or more pharmaceutically acceptable carriers, and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets (each containing a predetermined amount of the active ingredient); as a powder or granules; or as a solution, suspension or emulsion. The active ingredient may also be presented as a bolus, electuary or paste. Tablets and capsules for oral administration may contain conventional excipients such as binding agents, fillers, lubricants, disintegrants, or wetting agents. The tablets may be coated using methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds of the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis, the compounds of the invention may be formulated as ointments, creams or lotions, or as a transdermal patch. Such transdermal patches may contain penetration enhancers such as linalool, carvacrol, thymol, citral, menthol or t-anethole. Ointments and creams may, for example, be formulated with an aqueous or oily base with the addition of suitable thickening, and/or gelling, agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds of the invention may be provided in the form of a dry powder composition, for example a powder mix of the compound and a suitable powder base such as lactose or starch. The powder composition may be presented in unit dosage form in, for example, capsules or cartridges or, for example, gelatin or blister packs from which the powder may be administered with the aid of an inhalator or insufflator.

When desired, the above described formulations may be adapted to give sustained release of the active ingredient.

In a further embodiment, there is provided a combination useful for the treatment of thrombocythemia comprising at least one compound of formulas (I) through (III) and at least one further therapeutic agent chosen from anagrelide, hydroxyurea, $P^{32}$, busulphan, aspirin, clopidogrel, α-interferon, ticlopidine and dipyridamole.

In a further embodiment, there is provided a combination useful for the treatment of thrombocythemia comprising at least one compound of formulas (I) through (III) and at least one further therapeutic agent chosen from anagrelide, hydroxyurea, busulphan, and α-interferon.

The U.S. Provisional Application Ser. No. 60/598,432 (filed Aug. 4, 2004) and its Non-Provisional Application filed concurrently herewith, both directed to the compounds hereof for the treatment of peripheral arterial disease and inhibition of phosphodiesterase III, are incorporated herein by reference in their entireties.

The following examples are provided to illustrate various embodiments of the present invention and shall not be considered as limiting in scope.

EXAMPLE 1

Preparation of Compound #1 of the Present Invention

The Compound #1 N-(5,6-dichloro-3,4-dihydroquinazolin-2-yl)-2-oxoacetamide (1) having an m/z of 271 was synthesized. Compound #1 may also exist as its hydrate (2).

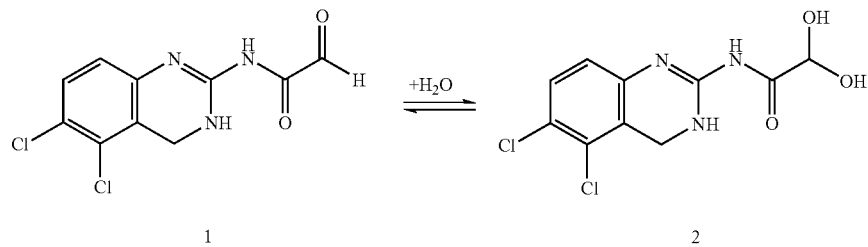

The combinations referred to above may conveniently be presented for use in the form of a pharmaceutical formulation; and, thus, pharmaceutical formulations comprising a combination as defined above together with a pharmaceutically acceptable carrier comprise a further embodiment of the invention.

The individual components of such combinations may be administered either sequentially or simultaneously in separate or combined pharmaceutical formulations.

When a compound of formulas (I) through (III), or an equilibrating form thereof, is used in combination with a second therapeutic agent, the dose of each compound may be either the same as or differ from that when the compound is used alone. Appropriate doses will be readily appreciated by those of ordinary skill in the art.

The ratio between the compounds of the present invention and the second therapeutic agent will be readily appreciated by those of ordinary skill in the art. For example, one may use from about 1:5000 to about 1:500, about 1:500 to about 1:100, about 1:1 to about 1:50, about 1:1 to about 1:30, about 1:1 to about 1:20, about 1:1 to about 1:15, about 1:1 to about 1:10, about 1:1 to about 1:5, or about 1:1 to about 1:3 of compounds of the invention:second therapeutic agent. If a further therapeutic agent is added, ratios will be adjusted accordingly.

Preparation of Compound #1

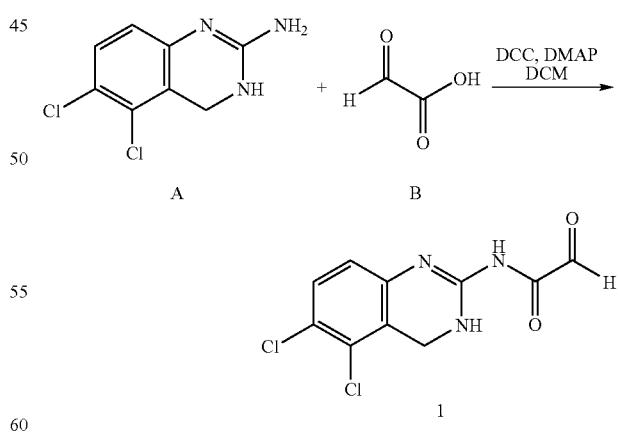

This approach to the required aldehyde (1) involved the reaction of 2-amino-5,6-dichloro-3,4-dihydroquinazoline (A) with glyoxalic acid hydrate (B) using a dicyclohexylcarbodiimide (DCC)-type coupling approach.

The coupling of (A) and glyoxalic acid (B) was conducted using dicyclohexylcarbodiimide (DCC), dimethylaminopyridine (DMAP) in dichloromethane (DCM). Product (A) can be obtained by methods known in the art (see, for example, U.S. Pat. No. 6,194,420, issued Feb. 27, 2001). A small amount of dimethylformamide (DMF) was added to aid the solubility of product. (A). When these reagents were mixed in the dichloromethane solvent, a precipitate formed. This precipitate was filtered and the solvent evaporated. This crude reaction mixture was analyzed by LC-MS, showing 90% starting material and 7% of material with a mass of 271.

This reaction was performed on a 150 mg scale. The precipitate formed (170 mg) in this reaction was collected and analyzed along with the contents of the filtrate. By LC-MS analysis the precipitate was comprised of two main components, product (A) (25% by peak area) and the material with a mass of 271 (66% by peak area); however, NMR analysis of the same material indicated that the major component was, in fact, dicyclohexylurea (DCU), the reacted form of the coupling agent DCC. Attempted purification of this material by HPLC resulted in removal of the DCU (as determined by NMR analysis), but gave a mixture of (A) (18% by peak area) and the material of mass 271 (73% by peak area). However, only one aromatic peak containing product was observed in the NMR spectrum.

Successful purification of Compound #1 was achieved using reverse phase chromatography. Gradient elution starting from water to methanol gave three distinct fractions: Firstly (A), secondly the material of mass 271, and finally the DCU (as determined by NMR and HPLC analysis).

As shown above, Compound #1 is an equilibrating form of Compound #3 and Compound #4. Therefore, as stated above, under the conditions of these examples, it is believed that the compounds are interconverting and that Compound #3 and Compound #4 (both known as 3-hydroxyanagrelide) are also present.

EXAMPLE 2

Alternative Synthesis of Compound #1

STEP 1

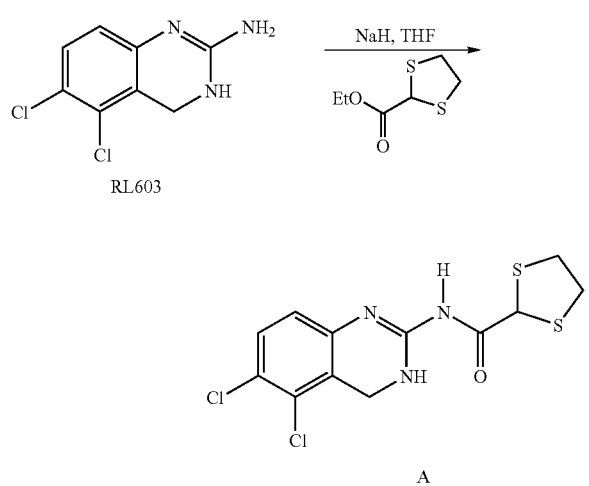

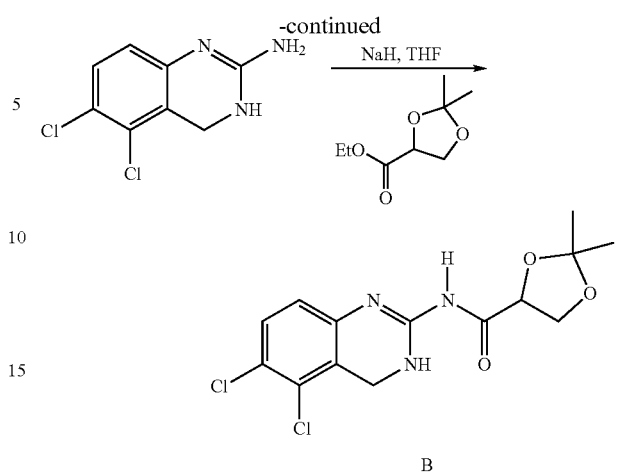

RL603 can be reliably acylated in modest to good yield by using 2.2 equivalents of sodium hydride and 1.1 equivalents of ethyl 2,3-isopropylidene glycerate to yield the product B (Scheme 1). The anion of RL603 was formed by heating with the sodium hydride in THF at 50° C. for 30 min under an inert atmosphere. Then the mixture was cooled to room temperature, the ester was added, and the reaction stirred for 3 days. Quick purification and usage of the products is preferable in order to avoid formation of fluorescent oxidized impurities. Purification was achieved by normal aqueous extraction and chromatography on silica (eluting with 40-50% ethyl acetate/ 60-50% petrol).

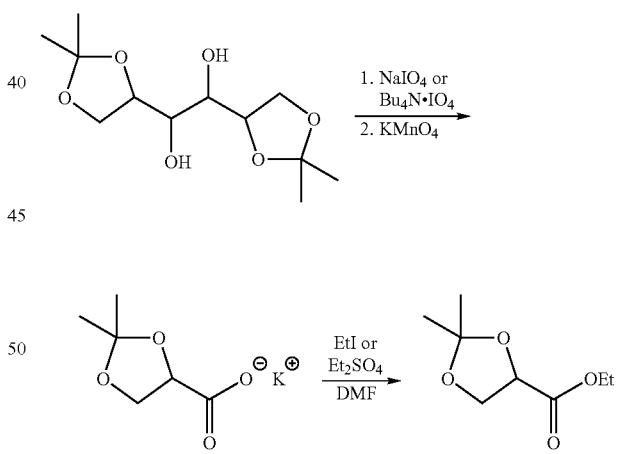

The ethyl 2,3-isopropylidene glycerate was prepared. 1,2: 5,6-Di-isopropylidene-mannitol was treated with either sodium periodate or tetra-butylammonium periodate followed by potassium permanganate to yield crude potassium isopropylidene-glycerate, which can be purified by recrystallization from ethanol. This was treated with preferably iodoethane or diethyl sulfate (the use of the latter makes it more difficult to recover the product) in DMF to form the ethyl ester (Scheme 2). The ester was then distilled if necessary.

STEP 2

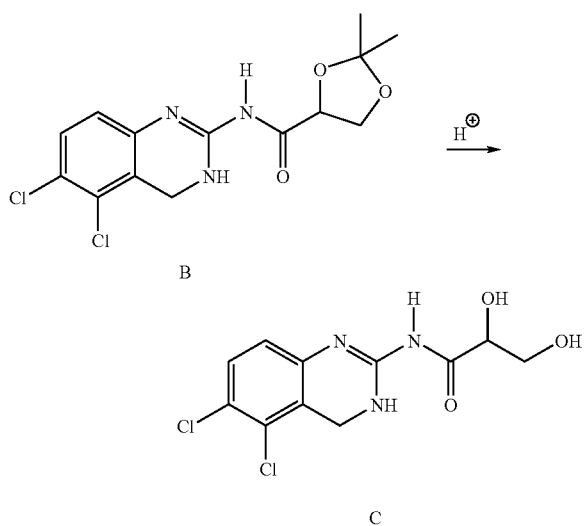

Scheme 3: Hydrolysis of compound B to compound C

Treatment of the acetal-acylated RL603 derivative B with 0.1 M HCl in a 50:50 mixture of water:THF overnight resulted in a roughly equal mixture of RL603 and the desired diol (C) (scheme 3). The use of 5:3 water:trifluoroacetic acid for one hour very cleanly and selectively gives the desired diol (C), requiring no purification except removal of the solvents.

STEP 3

Conversion of Compound (C) to Compound #1 and HPLC

Conversion of the diol (C) to Compound #1 was obtained by using sodium periodate in aqueous methanol or acetone. The diol was poorly soluble. Hydrolysis back to RL603 and formation of what appears to be an isomer of Compound #1 was noticed (it appears that this Iso-compound #1 is derived from the alternative mode of ring-closing of the intermediate aldehyde formed from periodate cleavage of diol (C).

Isomerisation of Compound #1 and Iso-compound #1 (a tautomer of Compound #5) are shown below:

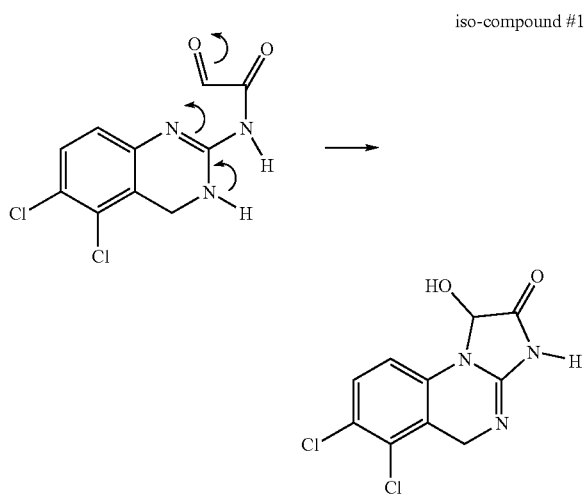

iso-compound #1

EXAMPLE 3

Evaluation of Compound #1 in Cultures of Differentiating Megakaryocytes Derived from Cord Blood CD3 4+ Cells Materials and Methods Chemicals. Compound #1 was kept at room temperature. Stock solutions (10 mM) were made in DMSO, or PBS pH 5. 0, as indicated. Stock solutions were diluted in culture medium immediately before addition to cell suspensions.

Cell Culture and Analysis of Megakaryocytic Differentiation.

Cell culture and drug regimes. Cord blood CD34+ cells were purchased from Biowhittacker USA or were freshly isolated by immunomagnetic selection using standard laboratory procedures. Cells were seeded in 24-well tissue culture plates at a density of $0.15 \times 10^6$ cells/ml and cultured for 12-14 days in Iscove's modified Dulbecco's medium containing 40 ng/ml TPO (as described in Mathur A, Hong Y. Martin J F, Erusalimsky J D (2001) *Megakaryocytic differentiation is accompanied by a reduction in cell migratory potential*. Br J Haematol 112:459) with anagrelide, Compound #1, or vehicle (DMSO).

Cell counting. Cell density was determined using a Sysmex CDA-500 Particle Analyzer.

Analysis of megakaryocytic differentiation. CD61 expression (a marker of megakaryocytic differentiation) was quantified by flow cytometry using an anti-GPIIIa antibody. Cell diameter was determined using a Sysmex CDA-500 Particle Analyzer.

Results

Evaluation of Compound #1 for TPO-Induced Megakaryocytic Maturation of CD34 Haematopoietic Progenitors The effects of anagrelide and Compound #1 on megakaryocytic maturation of CD34+ cells grown with thrombopoietin (TPO) in plasma-containing medium were assessed by recording the percentage of GPIIIa positive cells in the culture. Anagrelide and Compound #1 caused a significant inhibition of this process at concentrations as low as 30 nM (28% and 20% inhibition, P=0.004 and 0.005 for anagrelide and Compound #1 vs. control, respectively).

A close comparison between anagrelide and Compound #1 with regards to their activity against megakaryocyte maturation (FIG. 1) showed no significant difference between the two compounds when the effect of dose was considered (P=0.38 by ANOVA for Compound #1 vs. anagrelide). Indeed, the two compounds were equipotent, having an IC50-110-130 nM and a maximal effect at 1 μM. Results in FIG. 1 are expressed relative to an untreated sample run in parallel. Values represent the mean±standard error (SE) of 2-4 independent experiments as indicated. Each experiment was performed with cells derived from a different donor.

Overall effects of Compound #1 on in vitro Megakaryocytopoiesis

Table 1 shows that anagrelide and Compound #1 had substantial and similar inhibitory effects over a number of megakaryocyte differentiation parameters, including the final cell density, the proportion of GPIIIa positive cells, the relative level of expression of this antigen, and the cell size (the latter is a function of both cytoplasmic maturation and DNA content).

Figure 2:
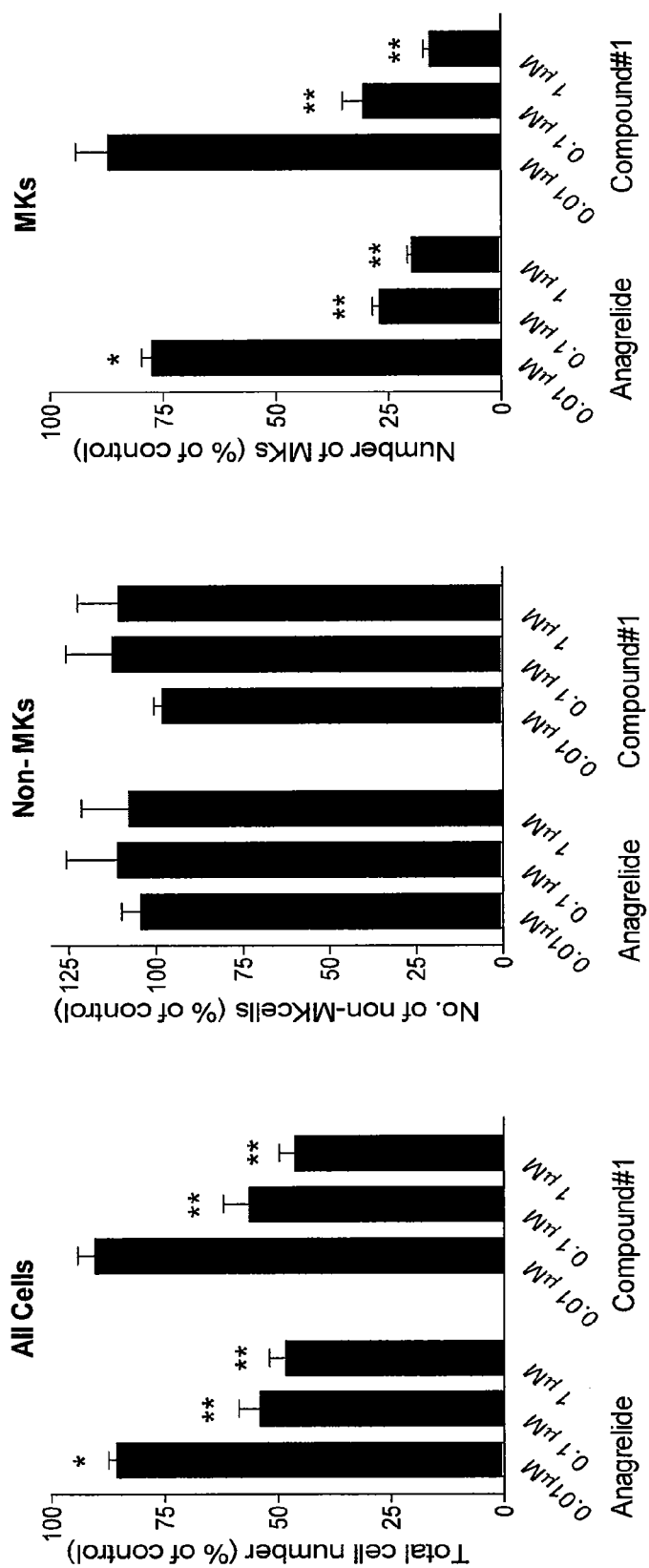
FIG. 2 is a graph comparing the selective inhibition of megakaryocytopoiesis by anagrelide and Compound #1 as more fully described in Example 3 below.

To assess whether the inhibitory activities of anagrelide and Compound #1 in these cultures were selective for the megakaryocytic lineage, the effects of these compounds were evaluated on the growth of the non-megakaryocytic cells. In 12-day control cultures these cells (CD61-) represent 20-30% of the total population. As depicted in FIG. 2, in sharp contrast to the reduction in the final number of cells expressing megakaryocytic features, neither anagrelide nor Compound #1 inhibited the growth of non-megakaryocytic cells.

TABLE 1

Effects of anagrelide and Compound #1 on megakaryocyte growth and differentiation parameters

| Drug | Cell expansion % of control | GPIIIa expression | | Relative cell size % of control |
|---|---|---|---|---|
| | | GPIIIa positive cells % of control | median fluorescence % of control | |
| Anagrelide (n = 4) | 48.0 ± 4.0 ** | 41.9 ± 6.6 ** | 51.3 ± 11.9 * | 80.4 ± 4.5 * |
| Compound #1 (n = 4) | 45.8 ± 3.9 ** | 34.5 ± 4.4 ** | 54.4 ± 14.7 * | 78.7 ± 5.3 * |

CD34+ cells were cultured for 12 days in plasma-containing medium supplemented with TPO in the presence or absence of the indicated compounds (1.0 μM) as described under Materials and Methods. Results of FIG. 2 are expressed relative to the untreated samples. Values represent the mean ± SE of the indicated number of independent experiments performed with cells derived from different donors.
* P < 0.05;
** P < 0.01 vs. control.

EXAMPLE 4

Synthesis 6,7-dichloro-3-hydroxy-1,5-dihydro-imidazo[2,1-b]quinazolin-2-one (compound#3)

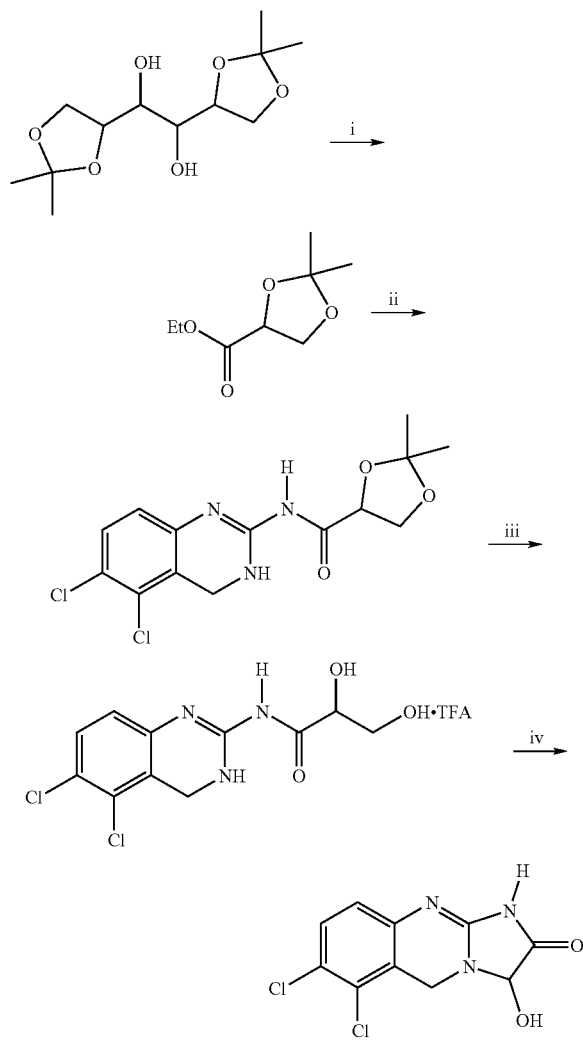

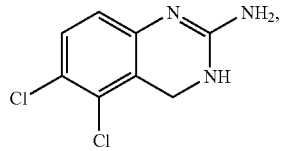

Reagents and Conditions:

Step (i): $KMnO_4$, KOH, water, room temperature (rt), 4 h, filter and evaporate, then DMF, ethyl iodide, rt, overnight, aqueous work-up, 56% yield overall.

Step (ii): 2-amino-5,6-dichloro-3,4-dihydroquinazoline,

NaH, THF, 50° C., 30 min, then rt, 48 h, aqueous work-up and column chromatography, 50% yield.

Step (iii): $CF_3CO_2H$, water, rt, 1 h, evaporate, freeze-dry and triturate with ether, 100% yield.

Step (iv): $NaIO_4$, pH 5.1 buffer, acetone, 10° C., 20 min, evaporate, freeze-dry and column chromatography, 31% yield.

Purification

Chromatographic isolation of product (resolution from the isomer compound#5 (6,7-Dichloro-1-hydroxy-3,5-dihydro-imidazo[1,2-a]quinazolin-2-one was performed on normal phase silica in a glass column under compressed air pressure, eluting with a gradient of 0-10% methanol/100-90% ethyl acetate. The fractions were analyzed by TLC (thin-layer chromatography) eluting with THF (tetrahydrofuran) containing a few drops of concentrated ammonia.

Analytical Data:

NMR $^1$H NMR (300 MHz, DMSO-$D_6$): 7.47 (1H, d, J=8.7 Hz), 6.96 (1H, d, J=8.7 Hz), 6.91 (1H, d, J=8.7 Hz), 5.01 (1H, d, J=6.7 Hz), 4.58+4.47 (2H, AB system, J=14.6 Hz).

$^{13}$C NMR (75 MHz, DMSO-$D_6$): 130.00, 129.49, 125.32, 120.41, 113.05, 81.29, 41.89 (Weak sample, some signals not resolved.)

Infra Red Spectroscopy

IR (neat): 1643, 1563, 1471 $cm^{-1}$.

Mass Spectroscopy (EI): 271 ($M^+$, 100%), 214 (86%), 199 (34%). %), 199 (35%)

Molecular Weight Determination

Hi-Res. MS: Calc. 270.991532. Found: 270.992371

Melting Point
M.p: 170° C. (dec.)

What is claimed is:

1. A substantially pure form of a compound of the formula:

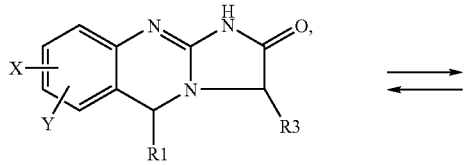

(II)

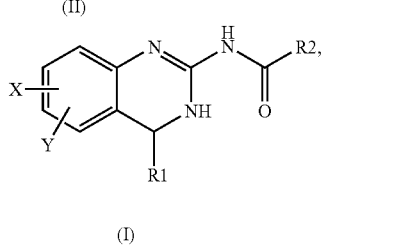

(I)

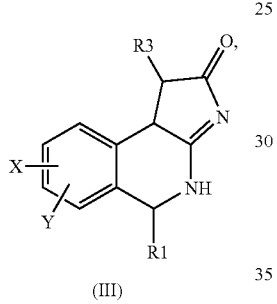

(III)

an equilibrating form thereof, or a pharmaceutically acceptable salt of the compound or of the equilibrating form thereof, wherein, R1 is H, $C_{1-6}$ alkyl, $C_{2-6}$ alkenyl, $C_{2-6}$ alkynyl, $C_{1-6}$ alkoxy, or $C_{6-10}$ aryl;

R2 is

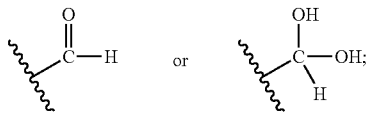

R3 is OH, SH; and

X and y are independently H or halogen.

2. A compound of claim 1, wherein the compound has the formula

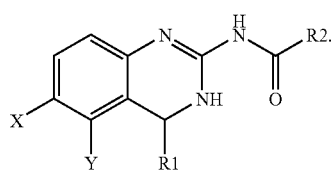

3. The compound of claim 2, wherein R2 is

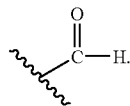

4. The compound of claim 2, wherein R1 is H or $C_{1-6}$ alkyl.
5. The compound of claim 2, wherein R1 is H.
6. The compound of claim 2, wherein X is H or halogen.
7. The compound of claim 2, wherein Y is H or Cl.
8. The compound of claim 2, wherein X is Cl.
9. The compound of claim 2, wherein Y is Cl.
10. The compound of claim 1, wherein the compound is

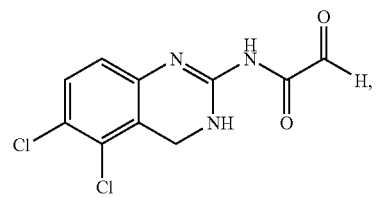

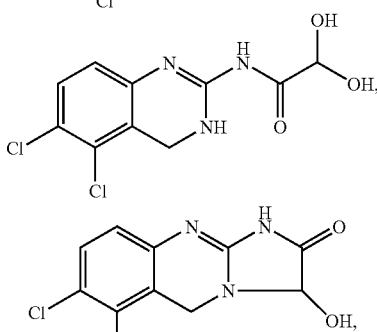

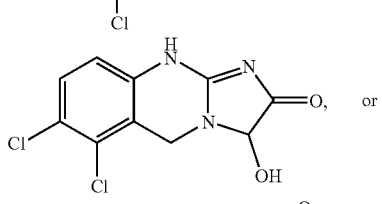

or

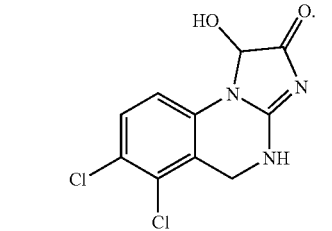

11. A method for the treatment of thrombocythemia comprising administering to a subject in need thereof a therapeutically effective amount of a compound of claim 1.

12. The method of claim 11, wherein the thrombocythemia is associated with essential thrombocythemia (ET), chronic myelogenous leukemia (CML), polycythemia vera (PV), agnogenic myeloid metaplasia (AMM) or sickle cell anemia (SCA).

13. A method for the treatment of thrombocythemia comprising administering to a subject in need thereof a therapeutically effective amount of a compound as defined in claim 10.

14. The method of claim 13 wherein the thrombocythemia is associated with essential thrombocythemia (ET), chronic myelogenous leukemia (CML), polycythemia vera (PV), agnogenic myeloid metaplasia (AMM) or sickle cell anemia (SCA).

15. A composition comprising at least one compound as defined in claim 1 and at least one therapeutic agent chosen from anagrelide, hydroxyurea, $P^{32}$, busulphan, aspirin, clopidogrel, α-interferon ticlopidine and dipyridamole.

16. A compound of claim 1, wherein R3 is OH.

17. A substantially pure compound of formula (II):

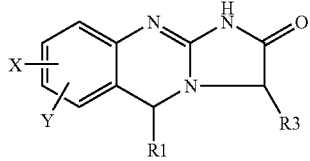

or a pharmaceutically acceptable salt of the compound, wherein

R1 is H, $C_{1-6}$alkyl, $C_{2-6}$alkenyl, $C_{2-6}$alkynyl, $C_{1-6}$alkoxy, or $C_{6-10}$aryl, R3 is OH or SH; and X and Y are independently H or halogen.

18. The compound of claim 17, wherein R1 is H, R3 is OH, X is Cl, and Y is Cl having for formula:

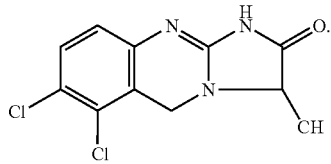

* * * * *